US011183285B2

(12) United States Patent
Lu et al.

(10) Patent No.: US 11,183,285 B2
(45) Date of Patent: Nov. 23, 2021

(54) MEDICATION DECISION SUPPORT

(71) Applicant: INTERNATIONAL BUSINESS MACHINES CORPORATION, Armonk, NY (US)

(72) Inventors: Fang Lu, Billerica, MA (US); Italo Buleje, Orlando, FL (US); Jingwei Yang, Cambridge, MA (US); Piyush Madan, Boston, MA (US); Rachita Chandra, Cambridge, MA (US); Sharon M. Hensley Alford, Dearborn, MI (US); Shilpa N. Mahatma, Chappaqua, NY (US); Sundar Saranathan, Framingham, MA (US)

(73) Assignee: International Business Machines Corporation, Armonk, NY (US)

( * ) Notice: Subject to any disclaimer, the term of this patent is extended or adjusted under 35 U.S.C. 154(b) by 224 days.

(21) Appl. No.: 15/854,059

(22) Filed: Dec. 26, 2017

(65) Prior Publication Data

US 2019/0198142 A1  Jun. 27, 2019

(51) Int. Cl.
*G16H 20/10* (2018.01)
*G16H 50/20* (2018.01)
*G16H 50/30* (2018.01)
*G16H 40/67* (2018.01)
*G16H 10/60* (2018.01)
*G16H 50/70* (2018.01)

(52) U.S. Cl.
CPC ............. *G16H 20/10* (2018.01); *G16H 40/67* (2018.01); *G16H 50/20* (2018.01); *G16H 50/30* (2018.01); *G16H 10/60* (2018.01); *G16H 50/70* (2018.01)

(58) Field of Classification Search
CPC ........ G16H 20/10; G16H 50/20; G16H 10/60; G16H 50/70
See application file for complete search history.

(56) References Cited

U.S. PATENT DOCUMENTS 9,044,188 B2 * 6/2015 DiLorenzo et al. . A61B 5/4094
2007/0219825 A1  9/2007 Maetzold et al.
(Continued)

OTHER PUBLICATIONS

Cancer Support Community NPL Reference, Treatment Options and Side Effects Management (Aug. 6, 2017) (available at: https://web.archive.org/web/20170806061610/https://www.cancersupportcommunity.org/treatment-options-and-side-effects-management (Year: 2017).*

(Continued)

*Primary Examiner* — Evangeline Barr
*Assistant Examiner* — Jordan L Jackson
(74) *Attorney, Agent, or Firm* — Kristofer L. Haggerty

(57) ABSTRACT

Embodiments of the present invention disclose a method, a computer program product, and a computer system for medication decision support. A computer generates one or more patient profiles detailing one or more patient health conditions and one or more medication profiles detailing one or more medication side effects. The computer then determines an association between the one or more patient health conditions and one or more medication side effects and quantifies the association as a conflict score. In addition, the computer determines whether the conflict score exceeds a threshold and, if so, the computer identifies and recommends an alternative medication having a lower conflict score.

11 Claims, 5 Drawing Sheets

(56) References Cited

U.S. PATENT DOCUMENTS

| | | | | |
|---|---|---|---|---|
| 2013/0179188 A1* | 7/2013 | Hyde | ............... | G06Q 10/10 |
| | | | | 705/3 |
| 2016/0321407 A1* | 11/2016 | Munoz-Jimenez | .... | G16H 70/40 |
| 2017/0124269 A1* | 5/2017 | McNair | ............... | G16H 10/60 |
| 2017/0308655 A1* | 10/2017 | Carlson | ............... | G16H 70/60 |

OTHER PUBLICATIONS

Willie Boag and Hassan Kané, AWE-CM Vectors: Augmenting Word Embeddings with a Clinical Metathesaurus, 31st Conference on Neural Information Processing Systems (Dec. 5, 2017) (Year: 2017).*

An Intuitive Understanding of Word Embeddings: From Count Vectors to Word2Vec, Analytics Vidhya (Jun. 4, 2017) (Year: 2017).*

B. Shickel, P. J. Tighe, A. Bihorac, and P. Rashidi, Deep ehr: A survey of recent advances in deep learning techniques for electronic health record (ehr) analysis, 22(5) IEEE Journal of Biomedical and Health Informatics 1589-1604 (first available Oct. 27, 2017) (Year: 2017).*

Distilled, "A Beginner's Guide to word2vec AKA What's the Opposite of Canada?", Resources (/resources/), https://www.distilled.net/resources/a-beginners-guide-to-word2vec-aka-whats-the-opposite-of-canada/, Printed on Oct. 12, 2017, pp. 1-10.

drugs.com, "Topiramate Side Effects," https://www.drugs.com/sfx/topiramate-side-effects.html, Printed on Oct. 12, 2017, pp. 1-5.

Textminer, "Text Mining Online: Getting Started with Keyword Extraction," http://textminingonline.com/getting-started-with-keyword-extraction, Posted on Nov. 1, 2015, Printed on Oct. 12, 2017, pp. 1-5.

Wikipedia, "Word2vec," https://en.wikipedia.org/wiki/Word2vec, Printed on Oct. 12, 2017, pp. 1-5.

Mell et al., "The NIST Definition of Cloud Computing," National Institute of Standards and Technology, U.S. Department of Commerce, Special Publication 800-145, Sep. 2011, pp. 1-7.

* cited by examiner

MEDICATION DECISION SUPPORT

BACKGROUND

The present invention relates generally to data analytics, and more particularly to providing medication decision support.

Even with the convenience of an electronic health record system, it can be difficult for a medical professional to ascertain the relationship between potential side effects of a particular medication set and a patient's medical, physical, mental, and psychological conditions.

SUMMARY

Embodiments of the present invention disclose a method, a computer program product, and a computer system for medication decision support with regard to patient side effects. A computer generates a patient profile and one or more medication profiles. The computer calculates a risk score for the patients medication regimen and determines whether the risk score exceeds a threshold value. Based on determining that the calculated risk score exceeds the threshold value, the computer modifies the patient medication regimen and re-calculates the medication regimen risk scores until the computer determines that the risk score does not exceed the threshold value.

More specifically, the method includes a computer generating a patient profile detailing one or more health conditions corresponding to a patient and a medication profile detailing one or more side effects corresponding to one or more medications taken by the patient. The method further includes the computing device calculating one or more conflict scores based on an association between the one or more health conditions and the one or more side effects.

The method may further include, based on the calculated conflict score exceeding a threshold value, the computer identifying one or more alternative medications having a same therapeutic effect as the one or more medications.

According to some embodiments, the method may further include suggesting replacement of the one or more medications with the one or more alternative medications. Moreover, the method may further comprise assigning a severity to each of the one or more health conditions based on comparing a normal level for each of the one or more health conditions to the patient level for each of the one or more health conditions. In addition, the method may further comprise determining a therapeutic value of the one or more medications, wherein the therapeutic value is based on an effectiveness rate of the one or more medications at treating the one or more health conditions.

According to another embodiment of the present invention, a computer program product for medication decision support is disclosed, the computer program product comprising one or more computer-readable storage devices and program instructions stored on at least one of the one or more tangible storage devices.

In such embodiments implementing a computer program product, the program instructions comprise program instructions to generate a patient profile detailing one or more health conditions corresponding to a patient, program instructions to generate a medication profile detailing one or more side effects corresponding to one or more medications taken by the patient, and program instructions to calculate one or more conflict scores based on an association between the one or more health conditions and the one or more side effects.

Additionally, according to some embodiments, the computer program product further includes, based on the calculated conflict score exceeding a threshold value, program instructions to identify one or more alternative medications having a same therapeutic effect as the one or more medications and program instructions to suggest replacement of the one or more medications with the one or more alternative medications In accordance with some embodiments, the computer program product may further comprise program instructions to assign a severity to each of the one or more health conditions, wherein the calculated conflict score is further based on the assigned severity. Additionally, in such embodiments, assigning the severity to each of the one or more health conditions further comprises program instructions to identify a normal level for each of the one or more health conditions, program instructions to identify a patient level for each of the one or more health conditions, and program instructions to compare the normal level to the patient level for each of the one or more health conditions.

In yet further embodiments, the computer program product further comprises program instructions to determine a therapeutic value of the one or more medications based on an effectiveness rate of the one or more medications at treating the one or more health conditions. In such embodiments, calculating the conflict score is further based on the determined therapeutic value.

Additionally disclosed in a computer system for medication decision support, the computer system comprising one or more processors, one or more computer-readable memories, one or more computer-readable tangible storage devices, and program instructions stored on at least one of the one or more storage devices for execution by at least one of the one or more processors via at least one of the one or more memories.

In such embodiments implementing a computer system, the program instructions comprise program instructions to generate a patient profile detailing one or more health conditions corresponding to a patient, program instructions to generate a medication profile detailing one or more side effects corresponding to one or more medications taken by the patient, and program instructions to calculate one or more conflict scores based on an association between the one or more health conditions and the one or more side effects.

Additionally, according to some embodiments, the computer system further includes, based on the calculated conflict score exceeding a threshold value, program instructions to identify one or more alternative medications having a same therapeutic effect as the one or more medications and program instructions to suggest replacement of the one or more medications with the one or more alternative medications In accordance with some embodiments, the computer system may further comprise program instructions to assign a severity to each of the one or more health conditions, wherein the calculated conflict score is further based on the assigned severity. Additionally, in such embodiments, assigning the severity to each of the one or more health conditions further comprises program instructions to identify a normal level for each of the one or more health conditions, program instructions to identify a patient level for each of the one or more health conditions, and program instructions to compare the normal level to the patient level for each of the one or more health conditions.

In yet further embodiments, the computer system further comprises program instructions to determine a therapeutic value of the one or more medications based on an effectiveness rate of the one or more medications at treating the one or more health conditions. In such embodiments, calculating the conflict score is further based on the determined therapeutic value.

BRIEF DESCRIPTION OF THE SEVERAL VIEWS OF THE DRAWINGS

The following detailed description, given by way of example and not intended to limit the invention solely thereto, will best be appreciated in conjunction with the accompanying drawings, in which.

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to implement such feature, structure, or characteristic in connection with other embodiments whether or not explicitly described.

In the interest of not obscuring the presentation of embodiments of the present invention, in the following detailed description, some processing steps or operations that are known in the art may have been combined together for presentation and for illustration purposes and in some instances may have not been described in detail. In other instances, some processing steps or operations that are known in the art may not be described at all. It should be understood that the following description is focused on the distinctive features or elements of various embodiments of the present invention.

Figure 1:
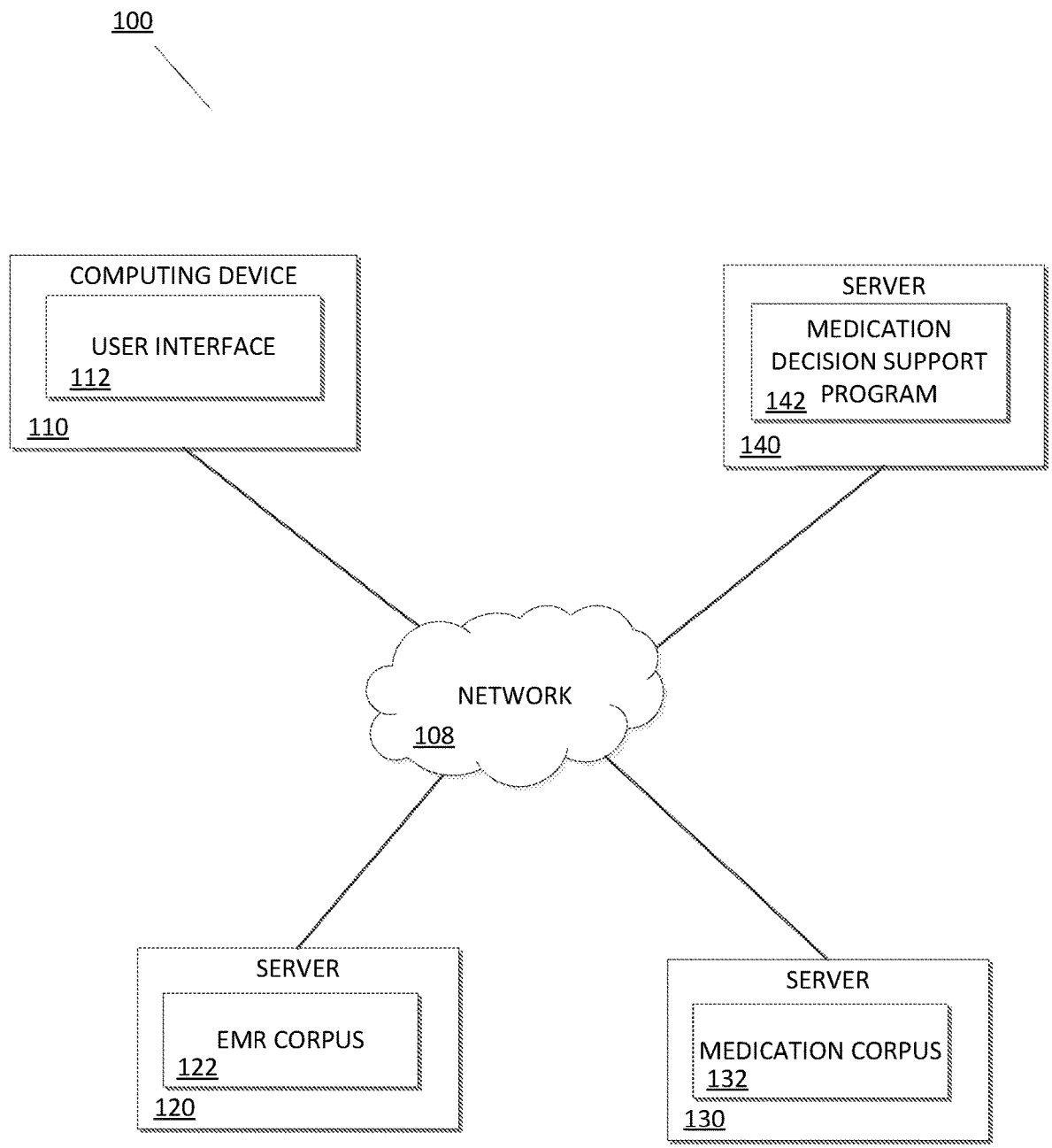
FIG. 1 depicts a schematic diagram of medication decision support system 100, in accordance with an embodiment of the present invention.

Medication decision support system 100 in accordance with an embodiment of the invention is illustrated by FIG. 1. In the example embodiment, medication decision support system 100 includes computing device 110, server 120, server 130, and server 140, all interconnected via network 108. While in the example embodiment, programming and data of the present invention are stored remotely across several servers via network 108, in other embodiments, programming and data of the present invention may be stored locally on as few as one physical computing device or, alternatively, amongst other computing devices than those depicted.

In the example embodiment, network 108 is a communication channel capable of transferring data between connected devices. In the example embodiment, network 108 may be the Internet, representing a worldwide collection of networks and gateways to support communications between devices connected to the Internet. Moreover, network 108 may include, for example, wired, wireless, or fiber optic connections which may be implemented as an intranet network, a local area network (LAN), a wide area network (WAN), or any combination thereof. In further embodiments, network 108 may be a Bluetooth network, a WiFi network, or a combination thereof. In yet further embodiments, network 108 may be a telecommunications network used to facilitate telephone calls between two or more parties comprising a landline network, a wireless network, a closed network, a satellite network, or any combination thereof. In general, network 108 can be any combination of connections and protocols that will support communications between computing device 110, server 120, server 130, and server 140.

In the example embodiment, computing device 110 includes user interface 112. Computing device 110 may be a laptop computer, a notebook, a tablet computer, a netbook computer, a personal computer (PC), a desktop computer, a personal digital assistant (PDA), a rotary phone, a touchtone phone, a smart phone, a mobile phone, a virtual device, a thin client, or any other electronic device or computing system capable of receiving and sending data to and from other computing devices. While computing device 110 is shown as a single device, in other embodiments, computing device 110 may be comprised of a cluster or plurality of computing devices, working together or working separately. Computing device 110 is described in more detail with reference to FIG. 3.

User interface 112 is a software application which allows a user of computing device 110 to interact with computing device 110 as well as other connected devices via network 108. In addition, user interface 112 may be connectively coupled to hardware components, such as those depicted by FIG. 3, for receiving user input, including mice, keyboards, touchscreens, microphones, cameras, and the like. In the example embodiment, user interface 112 is implemented via a web browsing application containing a graphical user interface (GUI) and display that is capable of transferring data files, folders, audio, video, hyperlinks, compressed data, and other forms of data transfer individually or in bulk. In other embodiments, user interface 112 may be implemented via other integrated or standalone software applications and hardware capable of receiving user interaction and communicating with other electronic devices.

In the example embodiment, server 120 includes electronic medical record (EMR) corpus 122 and may be a laptop computer, a notebook, a tablet computer, a netbook computer, a personal computer (PC), a desktop computer, a personal digital assistant (PDA), a rotary phone, a touchtone phone, a smart phone, a mobile phone, a virtual device, a thin client, or any other electronic device or computing system capable of receiving and sending data to and from other computing devices. While server 120 is shown as a single device, in other embodiments, server 120 may be comprised of a cluster or plurality of computing devices, working together or working separately. Server 120 is described in more detail with reference to FIG. 3.

EMR corpus 122 is a collection of information contained in files, folders, and other document types. In the example embodiment, EMR corpus 122 is a large collection of information that details a large number of patient electronic medical/health records. In other embodiments, however, EMR corpus 122 may detail bodies of categorized and subject specific data, such as legal, financial, medical, etc. data, or include uncategorized data of miscellaneous topics. In the example embodiment, EMR corpus 122 may be structured (i.e. have associated metadata), partially structured, or unstructured. Moreover, data within EMR corpus 122 may be written in programming languages of common file formats such as .docx, .doc, .pdf, .rtf, .jpg, .csv, .txt, etc. In further embodiments, EMR corpus 122 may include handwritten and other documents scanned or otherwise converted into electronic form. In the example embodiment, EMR corpus 122 includes patient medical records, or EMRs, which detail information such as patient gender, age, location, health conditions, etc. in electronic form.

In the example embodiment, server 130 includes medication corpus 132 and may be a laptop computer, a notebook, a tablet computer, a netbook computer, a personal computer (PC), a desktop computer, a personal digital assistant (PDA), a rotary phone, a touchtone phone, a smart phone, a mobile phone, a virtual device, a thin client, or any other electronic device or computing system capable of receiving and sending data to and from other computing devices. While server 130 is shown as a single device, in other embodiments, server 130 may be comprised of a cluster or plurality of computing devices, working together or working separately. Server 130 is described in more detail with reference to FIG. 3.

Medication corpus 132 is a collection of information contained in files, folders, and other document types. In the example embodiment, medication corpus 132 is a large collection of information that details prescription drugs and other medications. In other embodiments, however, medication corpus 132 may detail bodies of categorized and subject specific data, such as legal, financial, medical, etc. data, or include uncategorized data of miscellaneous topics. In the example embodiment, medication corpus 132 may be structured (i.e. have associated metadata), partially structured, or unstructured. Moreover, data within medication corpus 132 may be written in programming languages of common file formats such as .docx, .doc, .pdf, .rtf, .jpg, .csv, .txt, etc. In further embodiments, medication corpus 132 may include handwritten and other documents scanned or otherwise converted into electronic form. In the example embodiment, medication corpus 132 includes prescription drug information such as recommended dosage, restrictions, conflicts, etc. in electronic form.

In the example embodiment, server 140 includes medication decision support program 142. Server 140 may be a laptop computer, a notebook, a tablet computer, a netbook computer, a personal computer (PC), a desktop computer, a personal digital assistant (PDA), a rotary phone, a touchtone phone, a smart phone, a mobile phone, a virtual device, a thin client, or any other electronic device or computing system capable of receiving and sending data to and from other computing devices. While server 140 is shown as a single device, in other embodiments, server 140 may be comprised of a cluster or plurality of computing devices, working together or working separately. Server 140 is described in more detail with reference to FIG. 3.

In the example embodiment, medication decision support program 142 is a software application capable of generating one or more patient profiles detailing one or more patient health conditions and one or more medication profiles detailing one or more medication side effects. Medication decision support program 142 is further capable of determining an association between the one or more patient health conditions and one or more medication side effects. In addition, medication decision support program 142 is additionally capable of quantifying the determined association as a conflict score and determining whether the conflict score exceeds a threshold. If medication decision support program 142 determines that the conflict score exceeds the threshold, medication decision support program 142 is further capable of identifying and recommending an alternative medication having a lower conflict score.

Figure 2:
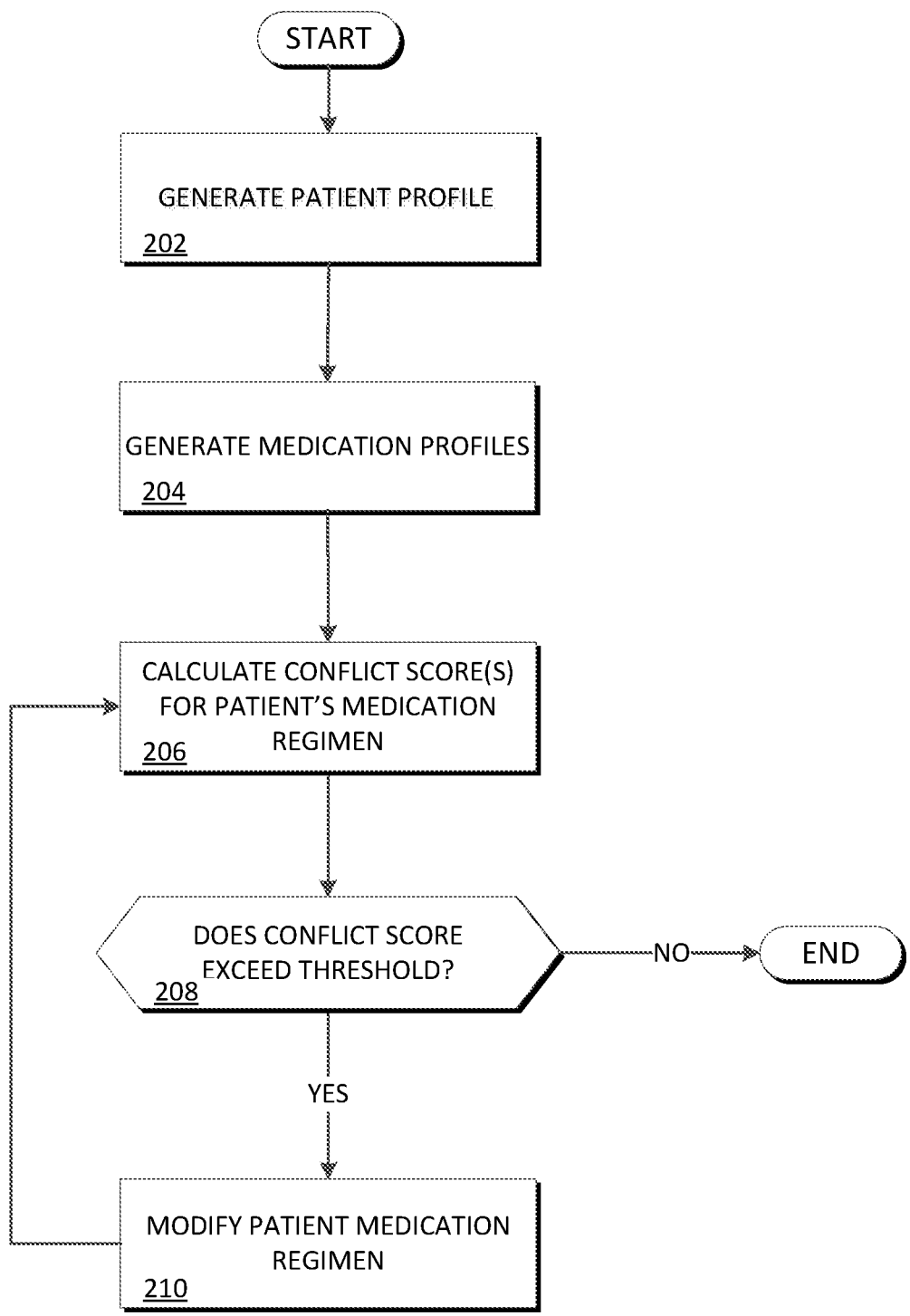
FIG. 2 depicts a flowchart illustrating the operations of medication decision support program 142 of medication decision support system 100 in providing medication decision support as it relates to identifying patient and medication conflicts, in accordance with an embodiment of the present invention.

FIG. 2 illustrates the operations of medication decision support program 142 of medication decision support system 100 in providing medication decision support with respect to patient condition and medication side effect conflicts. In the example embodiment, medication decision support program 142 generates and compares patient profiles to generated prescription drug profiles to identify a medication conflict where a side effect associated with a medication may aggregate or otherwise worsen the medical, mental, physical, etc., condition of a patient.

Medication decision support program 142 generates a patient profile corresponding to a patient (step 202). In the example embodiment, a patient profile is generated based on an associated EMR stored within EMR corpus 122 and accessed by medication decision support program 142 via network 108. For example, EMR corpus 122 may include websites and databases corresponding to insurance companies, hospitals, medical facilities, clinicians, federal agencies, and other entities that maintain records detailing general and/or health information of a person. In other embodiments, medication decision support program 142 may generate the patient profile based on patient data uploaded via user interface 112 of computing device 110 or reference to alternative corpora.

In the example embodiment (step 202 continued), medication decision support program 142 extracts health condition information for generation of the patient profile from the EMR via text analysis techniques such as template matching of known EMR formats and natural language processing in consideration of medical terminology. According to some embodiments, medication decision support program 142 may generate patient profiles for all patients contained in a database while, in other embodiments, medication decision support program 142 may generate patient profiles for only a class, subclass, or particular domain of patients. In addition to general and demographic information regarding a patient, such as patient gender, age, location, marital status, internet access availability, etc., the patient profile further details patient health conditions as they relate to medical, mental, physical, psychological, etc. conditions.

With reference to an illustrative example, medication decision support program 142 applies natural language processing techniques to a patient EMR to generate a patient profile detailing to a 60 year-old male living in New York who suffers from migraines, loss of hearing, glaucoma, and the early onset stages of Alzheimer's disease, to name a few.

In addition to detailing one or more conditions of a patient (step 202 continued), the patient profile further details a severity of the one or more conditions. In the example embodiment, the condition(s), the severity of the condition(s), and the risk of a medication side effect aggravating the condition(s) are taken into consideration in determining a conflict score, as will be described in much greater detail within the proceeding paragraphs. Having identified health conditions associated with a patient, medication decision support program 142 now determines a severity associated with each condition. In the example embodiment, severity is accounted for as a coefficient that weights the later-calculated risk score accordingly, for example weights ranging from 1 (low severity) to 5 (average severity) to 10 (high severity). In order to determine a severity of a condition associated with a patient, medication decision support program 142 references relational databases and other resources to determine an objective severity of the condition (e.g. normal levels for a comparable individual), then cross references the objective levels with the subjective severity of the patient (e.g. normal levels vs. patient levels). Based on the analysis described above, medication decision support program 142 determines a severity of the health conditions that is denoted by a coefficient associated with the particular condition.

With reference again to the illustrative example introduced above regarding a 60 year-old male suffering from migraines, medication decision support program 142 determines a severity of the patient's migraines by comparing a frequency of migraines for a typical 60 year-old male in similar health, as determined by analysing a cohort of similar 60 year-old male EMRs, to the frequency at which the 60 year-old male patient suffers from migraines, as determined by the specific patient EMR. For instance, medication decision support program 142 determines that a comparable individual experiences 1-2 migraines per month while the 60 year-old male suffers from 2-4 migraines per month (more frequent than average), and therefore assigns a high severity weight of 8 (on a scale from 1-10, 5 being average severity) to migraines within the patient profile. Conversely, if the 60 year-old male experiences 0-1 migraines per month (less frequent than average), then medication decision support program 142 assigns a low severity weight of 3 to the health condition migraines in the patient profile. Lastly, in cases where a patient experiences average severity or a severity is not detailed by an associated EMR, a default weight of 5 is applied.

Continuing the example above, medication decision support program 142 may further assess a severity not just by metrics such as frequency, but by other metrics such as a magnitude of the migraines as well. For example, if the EMR of the 60 year-old indicates that migraines result in near-paralysis or blindness of the patient, while a typical migraine for a comparable 60 year-old male results in discomfort or an inability to focus, then medication decision support program 142 assigns a high severity weight of 9 to migraines in the patient profile. In such embodiments in which a severity may be based on two or more factors (e.g. frequency and magnitude, as above), severity scores may be averaged, added, or multiplied based on the data analysis being implemented. For example, the severity score of 8 with regard to frequency and the severity score of 9 with regard to magnitude may be averaged to a final severity weight of 8.5, added to sum 17, etc. depending on the weight system selected. In general, the methods for determining a condition severity illustrated in the aforementioned example may be used in combination, alone, or with other severity weighting and assessment techniques when generating the patient profile. In the example embodiment, both the condition and the severity of the condition are used in computing an overall medication conflict score, as will be described in greater detail within the proceeding description.

In addition to determining a severity associated with migraines, medication decision support system further determines a severity associated with all conditions of detailed by the patient profile. In the example above and using similar methods, medication decision support program 142 further assigns a severity of 6 as it relates to the condition glaucoma, indicating that his condition is mildly more severe than average, and assigns both hearing loss and signs of Alzheimer's disease a severity of 5, indicating average severity for both.

Referring now back to FIG. 2, medication decision support program 142 generates a medication profile for one or more medications (step 204). In the example embodiment, the medication profile is generated based on pharmaceutical and research information stored within medication corpus 132 and accessed by medication decision support program 142 via network 108. For example, medication corpus 132 may include websites and databases corresponding to government agencies such as the Food and Drug Administration (FDA), research centres, educational institutions, hospitals, medical centres, clinics, labs, and any other resources which host information as it relates to medications and their side effects. In other embodiments, medication decision support program 142 may generate the medication profile based on medication information uploaded via user interface 112 of computing device 110 or reference to alternative corpora.

In the example embodiment (step 204 continued), medication decision support program 142 extracts information for generation of the medication profile from medication corpus 132 by applying text analysis techniques such as natural language processing and template matching to the prescription drug information within medication corpus 132. According to some embodiments, medication decision support program 142 may be configured to generate medication profiles for all medications identified in a database while, in other embodiments, medication decision support program 142 may be configured to generate medication profiles for a class, subclass, or particular domain of medications. In addition to general information regarding a particular medication, including recommended dosage, dosage frequency, restrictions, conflicts, suitable users, ingredients, etc., the medication profile further details known and, in some embodiments, suspected side effects associated with a medication. Moreover, the medication profile corresponding to a particular medication may further include information detailing other medications which, when taken in combination with the particular medication, are prone to cause side effects as well.

With reference to the earlier-introduced example, medication decision support program 142 extracts medication information from medication corpus 132 in order to identify side effects associated with one or more medications. For example, medication decision support program 142 generates a medication profile for Topiramate (Topamax) indicating that it is effective at relieving migraines, but is known to cause side effects such as blurred vision, confusion, and drowsiness. Moreover, medication decision support program 142 further determines and indicates that a dangerous drug interaction is possible when Topiramate is taken in combination with Monoamine oxidase inhibitors.

Medication decision support program 142 calculates conflict score(s) for the patient's medication regimen (step 206). In the example embodiment, the conflict score is generated based on the patient profile (health conditions, health condition severity), the medication profile (medication side effects), and a risk that the medication side effects will aggravate a patient health condition. More specifically, the conflict score is based on first determining a risk score that denotes a chance that a medication side effect will adversely affect a patient health condition, which is then weighted based on the severity score associated with the particular patient health condition affected by the side effect, as determined above. In the example embodiment, the risk score is first calculated based on analysing the health conditions detailed by a patient profile and the side effects detailed by the medication profiles of the medication regimen taken by the patient. In the present invention, the risk score is assigned per health condition and side effect combination and may be assessed retroactively for the current medication regimen of a patient or can be used proactively for assessment of future or proposed medication regimens of the patient.

In the example embodiment (step 206 continued), medication decision support program 142 may determine the risk scores using a variety of algorithms, such as Word2vec, in order to draw and quantify associations between medication side effects and patient health conditions. Word2vec is a group of related models that are used to produce word embedding's. Word2vec generates models that are shallow, two-layer neural networks that are trained to reconstruct linguistic contexts of words based on ingesting a large corpus of text and producing a vector space of several hundred dimensions. Word vectors are positioned in the vector space such that words that share common contexts are positioned in close proximity to one another in the space. Based on the distances between the words mapped in the vector space, medication decision support program 142 is capable of identifying associations between health conditions extracted from the patient profile and side effects extracted from the medication profiles. The associations are then quantified to output a side effect risk score corresponding to each side effect of the medications in the patients medication regimen, a medication risk score corresponding to all side effects of a particular medication, and medication regimen risk score corresponding to all medications in the patient medication regimen. In the example embodiment, the risk scores fall within a range, for example 1-10, and a greater risk score indicates an increased chance of a patient health condition being aggravated by a medication side effect.

With reference again to the illustrative example above, the medication regimen of the 60 year-old male suffering from migraines may include Topimirate (Topamax) to combat migraines. Accordingly, medication decision support program 142 utilizes the algorithm Word2vec in order to identify associations between the patient health conditions (migraines, hearing loss, glaucoma, and early stages of Alzheimer's) and Topiramate side effects (blurred vision, confusion, and drowsiness). More specifically, medication decision support program 142 calculates a side effect risk score of 7 based on the identified association between glaucoma and blurred vision as well as a side effect risk score of 6 based on the identified association between confusion and early stage of Alzheimer's disease. Lastly, medication decision support program 142 assigns a side effect risk score of 0 to drowsiness, indicating that the side effect is not aggravated by any Topiramate side effects. In some embodiments, medication decision support program 142 may further determine a medication risk score for Topiramate which comprises an aggregate of the side effect risk scores, i.e. 13. In embodiments wherein the patient regimen includes multiple medications, medication decision support program 142 may further determine a medication regimen risk score comprising an aggregate of the medication risk scores in a patient medication regimen.

Medication decision support program 142 then determines the conflict score based on modifying the risk score in accordance with the severity weight associated with each of the patients health conditions (step 206 continued). In the example embodiment, the conflict score is calculated by multiplying the risk score by the severity score for that particular patient condition. In other embodiments, however, incorporation of severity may be performed via alternative means or, in some embodiments, severity may be excluded from the analysis.

With reference again to the example above wherein the patient profile of the 60 year-old male indicates a high severity of 8 to migraines, a normal severity of 5 to hearing loss and Alzheimer's disease, and a slightly high sensitivity of 6 to glaucoma, medication decision support program 142 first multiples the side effect risk scores by the severity scores to determine a conflict score for each medication side effect. Because hearing loss aggravation is not associated with any side effects of Topiramate, calculation of a side effect conflict score for hearing loss is omitted in the example embodiment. Thus, medication decision support program 142 determines a side effect conflict score for glaucoma by multiplying the side effect risk score of blurred vision, i.e. 7, by the severity score of glaucoma, i.e. 6 (slightly above average), for a side effect conflict score of 42. Similarly, medication decision support program 142 determines a side effect conflict score for Alzheimer's disease by multiplying the side effect risk score of 6 by the severity score of 5 for a side effect conflict score of 30. In some embodiments, individual conflict scores may be summed for a medication conflict score corresponding to all side effects of a particular medication. In the example above, for instance, medication decision support program 142 would assign Topiramate a medication conflict score of 72 (i.e. 42+30). In addition, medication decision support program 142 may further determine a medication regimen conflict score by adding the medication conflict scores of all medications within the medication regimen of the patient.

It is important to note that in some embodiments, a high conflict score, and even a conflict score in excess of a conflict score threshold as described below, may be tolerable in particular circumstances. In such embodiments, a high conflict score may be tolerated or disregarded because a therapeutic effect of a medication outweighs a side effect conflict. For example, the use of chemotherapy may result in a high chance of side effects such as hair loss, amongst others, however because it addresses a highly severe and dangerous health condition of cancer, it may be tolerable. In the previously introduced example, for instance, Topiramate is used to address migraines which, according to the patient profile, is a severe patient health condition, however will likely aggravate patient conditions glaucoma and Alzheimer's disease. In some embodiments, the health condition being addressed by the medication may be considered when determining whether a conflict score is tolerable similar to the manner in which severity is incorporated into the conflict score. In such embodiments, medication decision support program 142 may reference medication corpus 132 to assess an estimated success rate of a particular medication and multiply the estimated success rate by the severity of the health condition it addresses, thereby calculating what may be referred to as a therapeutic value. For example, if Topiramate is estimated to be 50% effective at reducing migraines in comparable individuals, and the patient migraine severity score is 8, then medication decision support program 142 calculates a therapeutic value of 4 that may counteract the conflict score. In such embodiments, the therapeutic value may be calculated in a variety of manners, and may be simply subtracted from the conflict score or accounted for in via other means. Using the example above, the Topiramate medication conflict score of 72 may be reduced by the therapeutic value of 4 to 68.

Medication decision support program 142 determines whether the calculated conflict score(s) exceed a predefined conflict score threshold (decision 208). In the example embodiment, medication decision support program 142 may be programmed to apply a conflict score threshold defining a maximum allowable side effect conflict score, medication conflict score, and/or medication regimen conflict score. In the example embodiment, conflict scores exceeding the conflict score threshold prompt a suggestion to a user of medication decision support program 142 to seek an alternative medication to the medication(s) exceeding or contributing to exceed the conflict score threshold. In other embodiments, however, conflict scores exceeding the conflict score threshold may automatically substitute an alternative medication in the patients medication regimen.

With reference again to the example above, if medication decision support program 142 is configured to compare side effect conflict scores to a side effect conflict score threshold of, for example, 25, then medication decision support program 142 compares the side effect conflict scores of 42 and 30 to the side effect conflict threshold of 25 to determine that the side effects of Topiramate (i.e. blurred vision and confusion) exceed the conflict score threshold. Alternatively, if medication decision support program 142 is configured to compare medication conflict scores to the medication conflict score threshold of, for example 50, then medication decision support program 142 determines that the conflict score of the medication Topiramate of 72 exceeds the medication conflict score threshold of 50. Lastly, in embodiments wherein a patient's medication regimen includes multiple medications, medication decision support program 142 may be configured to compare a medication regimen conflict score to a medication regimen conflict score threshold.

If medication decision support program 142 determines that the conflict score(s) exceeds the conflict score threshold (decision 208 "YES" branch), then medication decision support program 142 modifies the medication regimen of the patient. In the example embodiment, medication decision support program 142 modifies the medication regimen by seeking an alternative medication to medications whose side effect or medication conflict score exceeds the respective conflict score thresholds. In cases wherein the medication regimen conflict score exceeds a medication regimen conflict score threshold, medication decision support program 142 then analyses the regimen to determine which medications for which to find alternatives. In some embodiments, medication decision support program 142 may be configured to determine alternative medications to those having a side effect with a highest side effect risk score or side effect conflict score. In other embodiments, medication decision support program 142 may be configured to determine alternative medications to those having a side effect most related to the patients most severe condition(s). Overall, medication decision support program 142 may implement many different techniques for determining which and how many medications of a patient medication regimen in order to reduce risk scores to appropriate levels.

In order to identify alternative medications, medication decision support program 142 searches the medication profiles stored in medication corpus 132 for a medication having a same therapeutic effect with less of or without the associated high risk, severity, conflict, etc. As used herein, a same therapeutic effect may be any other medication that is intended for and treats a same or similar health condition. In some embodiments, medication decision support program 142 may be configured to reference previous regimens of the patient and/or other similar patients to determine an alternative medication that is most effective at mitigating the risk of a patient condition associated with highest severity, risk, conflict score, etc. In addition or alternatively, medication decision support program 142 may make recommendations as to how the side effects can be better managed by the patient with suggestions for accommodating the side effects, such as ensuring a family member is around to drive the patient or keeping other medications on hand.

In the example above, medication decision support program 142 identifies blurred vision as the side effect which most exacerbates the patient's health condition, glaucoma, and searches corpus 124 for alternative prescription drugs having the therapeutic relief for migraines without causing blurred vision to identify the medication prescription extra strength ibuprofen. In some embodiments, medication decision support program 142 will select an alternative medication that relieves the intended patient condition which has a least amount of side effects which effect a patients other health conditions. In other embodiments, medication decision support program 142 selects an alternative medication that isn't associated with the side effect having a highest side effect severity, risk, or conflict score. In yet further embodiments, a balance may be struck which considers all alternative medications and side effects to find a compromise between therapeutic value and conflict score. Such a balance may be further constrained via user input through selection of particular side effects, particular alternative medications, maximum allowable risks/conflicts, and the like.

Medication decision support program 142 recalculates the conflict score(s) for the patients modified medication regimen (step 206). In the example embodiment, medication decision support program 142 recalculates the conflict score(s) in much the same manner as above, however in this case medication decision support program 142 calculates the conflict score(s) in consideration of the modifications made to the patient medication regimen.

With reference again to the example above, medication decision support program 142 calculates new conflict scores for the prescription extra strength ibuprofen, reflecting the removal of Topiramate from the patient mediation regimen and addition of prescription extra strength ibuprofen.

If medication decision support program 142 determines that the calculated risk score(s) do not exceed the conflict score threshold (decision 208 "NO" branch), then medication decision support program 142 ends.

Referring to the example above, based on medication decision support program 142 determining that the modified medication regimen risk score(s) do not exceed the conflict score threshold(s), medication decision support program 142 ends.

Figure 3:
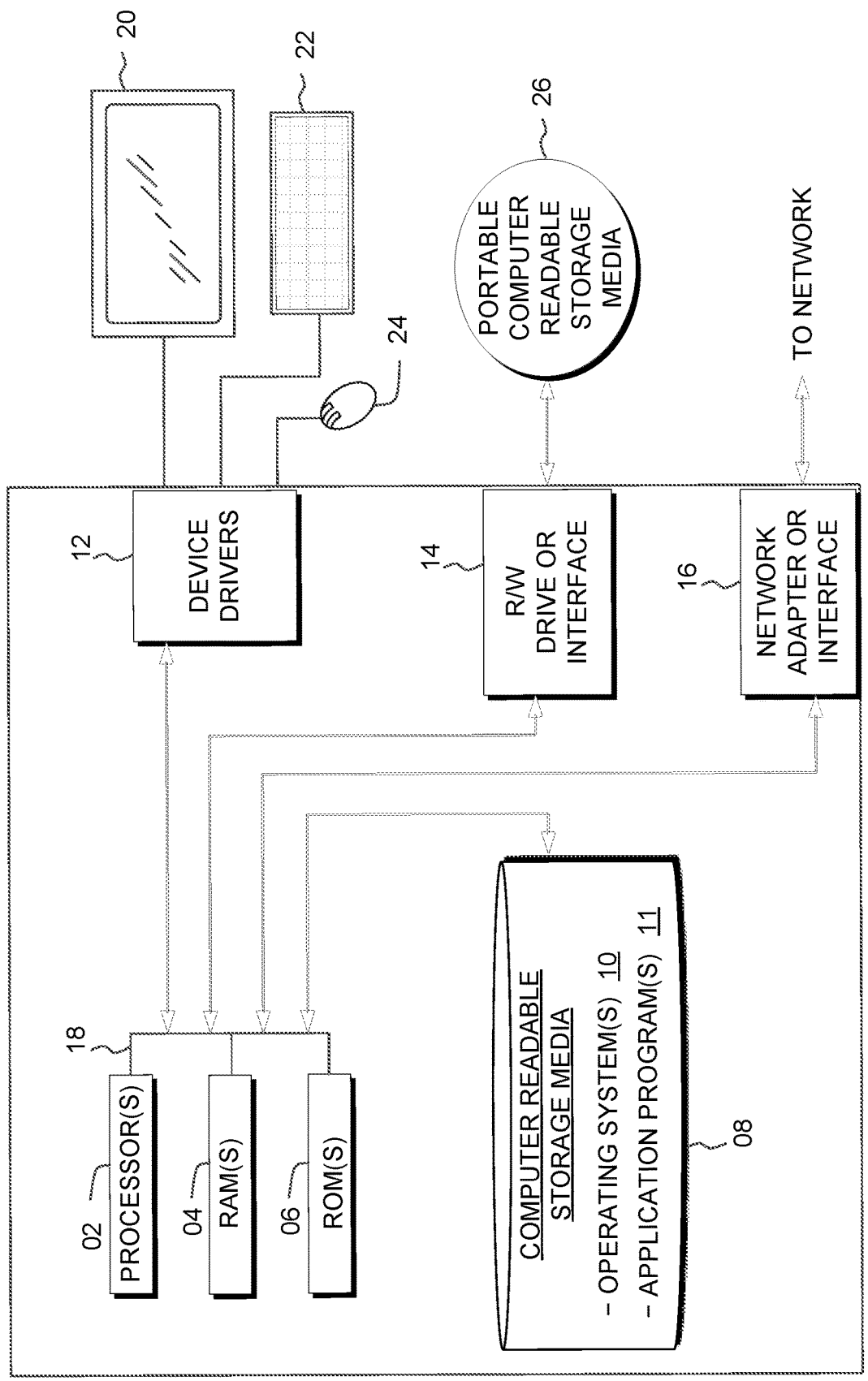
FIG. 3 depicts a block diagram depicting the hardware components of medication decision support system 100 of FIG. 1, in accordance with an embodiment of the present invention.

FIG. 3 depicts a block diagram of computing device 110, server 120, server 130, and server 140 of medication decision support system 100 of FIG. 1, in accordance with an embodiment of the present invention. It should be appreciated that FIG. 3 provides only an illustration of one implementation and does not imply any limitations with regard to the environments in which different embodiments may be implemented. Many modifications to the depicted environment may be made.

Computing device 110 may include one or more processors 02, one or more computer-readable RAMs 04, one or more computer-readable ROMs 06, one or more computer readable storage media 08, device drivers 12, read/write drive or interface 14, network adapter or interface 16, all interconnected over a communications fabric 18. Communications fabric 18 may be implemented with any architecture designed for passing data and/or control information between processors (such as microprocessors, communications and network processors, etc.), system memory, peripheral devices, and any other hardware components within a system.

One or more operating systems 10, and one or more application programs 11, for example medication decision support program 142, are stored on one or more of the computer readable storage media 08 for execution by one or more of the processors 02 via one or more of the respective RAMs 04 (which typically include cache memory). In the illustrated embodiment, each of the computer readable storage media 08 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Computing device 110 may also include a R/W drive or interface 14 to read from and write to one or more portable computer readable storage media 26. Application programs 11 on said devices may be stored on one or more of the portable computer readable storage media 26, read via the respective R/W drive or interface 14 and loaded into the respective computer readable storage media 08.

Computing device 110 may also include a network adapter or interface 16, such as a TCP/IP adapter card or wireless communication adapter (such as a 4G wireless communication adapter using OFDMA technology). Application programs 11 on said computing devices may be downloaded to the computing device from an external computer or external storage device via a network (for example, the Internet, a local area network or other wide area network or wireless network) and network adapter or interface 16. From the network adapter or interface 16, the programs may be loaded onto computer readable storage media 08. The network may comprise copper wires, optical fibers, wireless transmission, routers, firewalls, switches, gateway computers and/or edge servers.

Computing device 110 may also include a display screen 20, a keyboard or keypad 22, and a computer mouse or touchpad 24. Device drivers 12 interface to display screen 20 for imaging, to keyboard or keypad 22, to computer mouse or touchpad 24, and/or to display screen 20 for pressure sensing of alphanumeric character entry and user selections. The device drivers 12, R/W drive or interface 14 and network adapter or interface 16 may comprise hardware and software (stored on computer readable storage media 08 and/or ROM 06).

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Based on the foregoing, a computer system, method, and computer program product have been disclosed. However, numerous modifications and substitutions can be made without deviating from the scope of the present invention. Therefore, the present invention has been disclosed by way of example and not limitation.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 4:
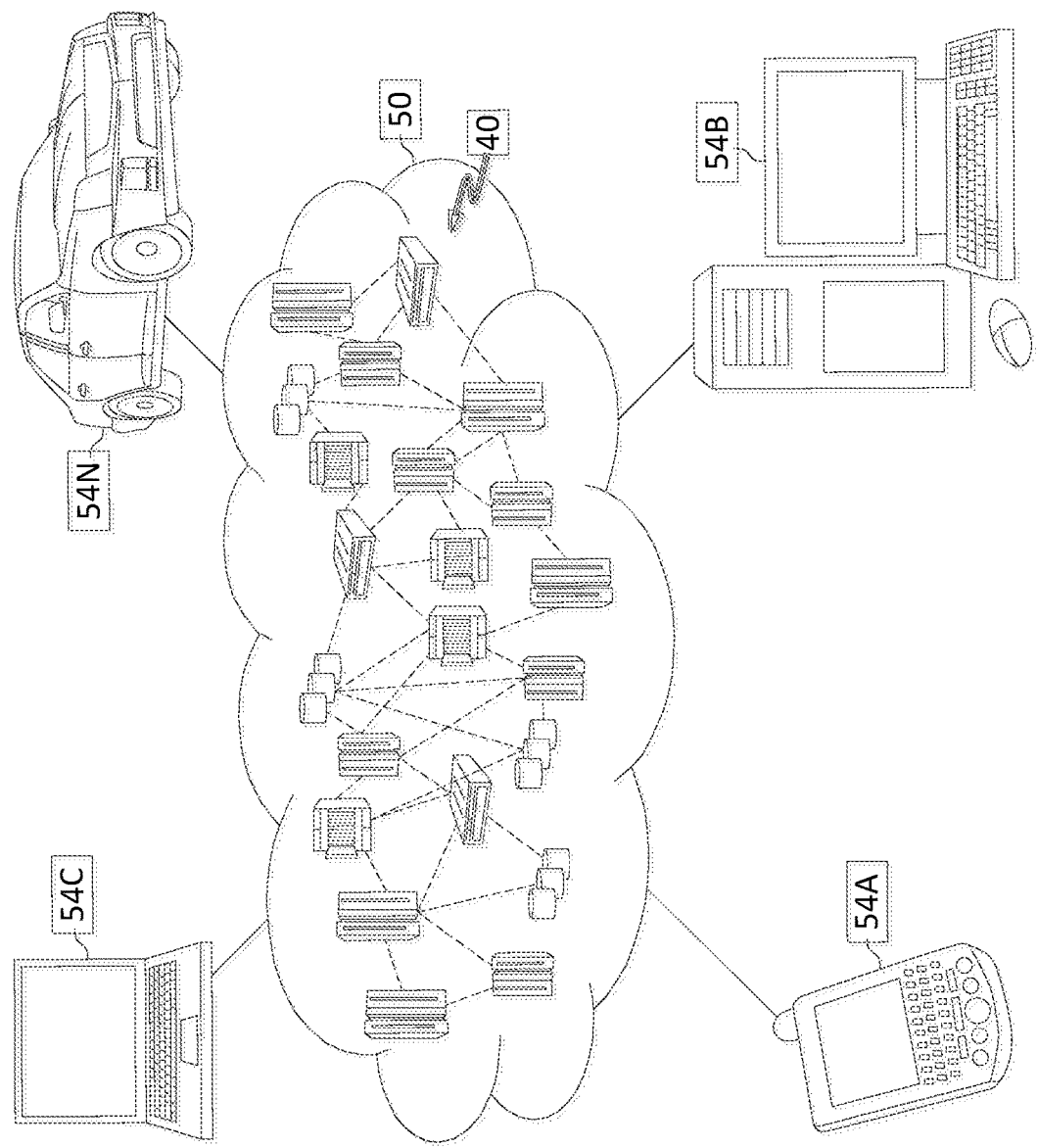
FIG. 4 depicts a cloud computing environment, in accordance with an embodiment of the present invention.

Referring now to FIG. 4, illustrative cloud computing environment 50 is depicted. As shown, cloud computing environment 50 includes one or more cloud computing nodes 40 with which local computing devices used by cloud consumers, such as, for example, personal digital assistant (PDA) or cellular telephone 54A, desktop computer 54B, laptop computer 54C, and/or automobile computer system 54N may communicate. Nodes 40 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 40 and cloud computing environment 50 can communicate with any type of computerized device over any type of network and/or network addressable connection (e.g., using a web browser).

Figure 5:
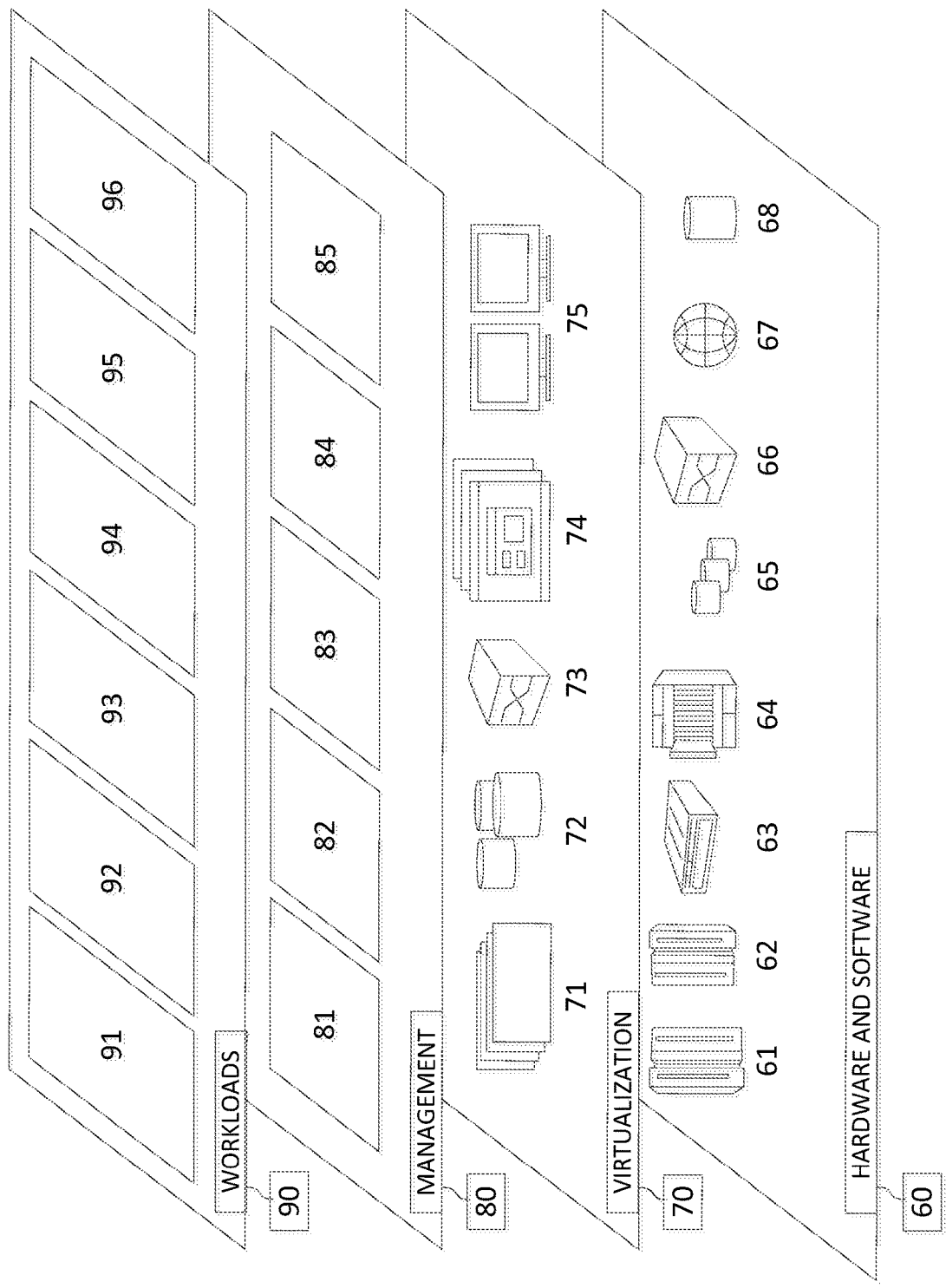
FIG. 5 depicts abstraction model layers, in accordance with an embodiment of the present invention.

Referring now to FIG. 5, a set of functional abstraction layers provided by cloud computing environment 50 (FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and medication decision support processing 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A method for medication decision support, the method comprising:
    a computer ingesting data detailing one or more health conditions of a patient and one or more side effects of one or more medications taken by the patient, wherein the one or more side effects include those exhibited when the one or more medications are taken in combination;
    the computer training one or more models to reconstruct linguistic contexts of words within a vector space of several hundred dimensions;
    the computer reconstructing a linguistic context of the data using the one or more models;
    the computer calculating one or more conflict scores between the one or more health conditions and the one or more side effects based on calculating a distance between two or more vectors representing distances between the linguistic context of the data within the vector space;

the computer assigning a severity score to each of the one or more health conditions, wherein the conflict score is further based on the severity score, and wherein the severity score is based on comparing a frequency and a magnitude of the one or more health conditions experienced by the patient to a frequency and a magnitude of the one or more health conditions experienced by another patient;

based on the calculated one or more conflict scores exceeding a threshold value, the computer identifying one or more alternative medications for treating a same health condition;

the computer calculating one or more alternative conflict scores between the one or more health conditions and the one or more side effects of the one or more alternative medications, wherein the one or more alternative conflict scores are further based on the severity score; and based on the calculated one or more alternative conflict scores failing to exceed the threshold value, the computer substituting the one or more medications with the one or more alternative medications.

2. The method of claim 1, further comprising:
the computer providing one or more recommendations for managing the one or more side effects.

3. The method of claim 1, further comprising:
determining a therapeutic value of the one or more medications, and wherein calculating the conflict score is further based on the determined therapeutic value.

4. The method of claim 3, wherein determining the therapeutic value is based on an effectiveness rate of the one or more medications at treating the one or more health conditions.

5. A computer program product for medication decision support, the computer program product comprising:
one or more computer-readable, non-transitory storage devices and program instructions stored on at least one of the one or more tangible storage devices, the program instructions comprising:
program instructions to ingest data detailing one or more health conditions of a patient and one or more side effects of one or more medications taken by the patient, wherein the one or more side effects include those exhibited when the one or more medications are taken in combination;
program instructions to train one or more models to reconstruct linguistic contexts of words within a vector space of several hundred dimensions;
program instructions to reconstruct a linguistic context of the data using the one or more models;
program instructions to calculate one or more conflict scores between the one or more health conditions and the one or more side effects based on calculating a distance between two or more vectors representing distances between the linguistic context of the data within the vector space;
program instructions to assign a severity score to each of the one or more health conditions, wherein the conflict score is further based on the severity score, and wherein the severity score is based on comparing a frequency and a magnitude of the one or more health conditions experienced by the patient to a frequency and a magnitude of the one or more health conditions experienced by another patient;
based on the calculated one or more conflict scores exceeding a threshold value, program instructions to identify one or more alternative medications for treating a same health condition;
program instructions to calculate one or more alternative conflict scores between the one or more health conditions and the one or more side effects of the one or more alternative medications, wherein the one or more alternative conflict scores are further based on the severity score; and
based on the calculated one or more alternative conflict scores failing to exceed the threshold value, program instructions to substitute the one or more medications with the one or more alternative medications.

6. The computer program product of claim 5, further comprising:
program instructions to provide one or more recommendations for managing the one or more side effects.

7. The computer program product of claim 5, further comprising:
program instructions to determine a therapeutic value of the one or more medications, and wherein calculating the conflict score is further based on the determined therapeutic value.

8. The computer program product of claim 7, wherein determining the therapeutic value is based on an effectiveness rate of the one or more medications at treating the one or more health conditions.

9. A computer system for medication decision support, the computer system comprising:
one or more processors, one or more computer-readable memories, one or more computer-readable tangible storage devices, and program instructions stored on at least one of the one or more storage devices for execution by at least one of the one or more processors via at least one of the one or more memories, the program instructions comprising:
program instructions to ingest data detailing one or more health conditions of a patient and one or more side effects of one or more medications taken by the patient, wherein the one or more side effects include those exhibited when the one or more medications are taken in combination;
program instructions to train one or more models to reconstruct linguistic contexts of words within a vector space of several hundred dimensions;
program instructions to reconstruct a linguistic context of the data using the one or more models;
program instructions to calculate one or more conflict scores between the one or more health conditions and the one or more side effects based on calculating a distance between two or more vectors representing distances between the linguistic context of the data within the vector space;
program instructions to assign a severity score to each of the one or more health conditions, wherein the conflict score is further based on the severity score, and wherein the severity score is based on comparing a frequency and a magnitude of the one or more health conditions experienced by the patient to a frequency and a magnitude of the one or more health conditions experienced by another patient;
based on the calculated one or more conflict scores exceeding a threshold value, program instructions to identify one or more alternative medications for treating a same health condition;
program instructions to calculate one or more alternative conflict scores between the one or more health conditions and the one or more side effects of the one or more alternative medications, wherein the one or more alternative conflict scores are further based on the severity score; and based on the calculated one or more alternative conflict scores failing to exceed the threshold value, program instructions to substitute the one or more medications with the one or more alternative medications.

10. The computer system of claim 9, further comprising:
program instructions to provide one or more recommendations for managing the one or more side effects.

11. The computer system of claim 9, further comprising:
program instructions to determine a therapeutic value of the one or more medications, and wherein calculating the conflict score is further based on the determined therapeutic value.

* * * * *